United States Patent
Pruvot et al.

(10) Patent No.: US 8,489,173 B2
(45) Date of Patent: Jul. 16, 2013

(54) CT TOMOGRAPHIC IMAGING PROCESS AND SYSTEM

(75) Inventors: Celine Pruvot, Buc (FR); Laurent Launay, St. Remy les Chevreuse (FR)

(73) Assignee: General Electric Company, Schenectady, NY (US)

(*) Notice: Subject to any disclaimer, the term of this patent is extended or adjusted under 35 U.S.C. 154(b) by 855 days.

(21) Appl. No.: 12/151,941

(22) Filed: May 9, 2008

(65) Prior Publication Data

US 2008/0279779 A1 Nov. 13, 2008

(30) Foreign Application Priority Data

May 11, 2007 (FR) .................................... 07 55012

(51) Int. Cl.
*A61B 5/05* (2006.01)
*G06K 9/00* (2006.01)

(52) U.S. Cl.
USPC .......................................... 600/410; 382/128

(58) Field of Classification Search
USPC ................... 600/410; 382/128, 131; 378/62, 378/63
See application file for complete search history.

(56) References Cited

U.S. PATENT DOCUMENTS

| | | | |
|---|---|---|---|
| 4,079,730 A * | 3/1978 | Wikswo et al. | 600/504 |
| 6,593,101 B2 * | 7/2003 | Richards-Kortum et al. | 435/29 |
| 6,628,743 B1 * | 9/2003 | Drummond et al. | 378/8 |
| 6,888,916 B2 * | 5/2005 | Launay et al. | 378/8 |
| 7,346,202 B1 * | 3/2008 | Schneider | 382/128 |
| 7,715,609 B2 | 5/2010 | Rinck et al. | |
| 7,738,701 B2 * | 6/2010 | Matsumoto | 382/173 |
| 7,925,330 B2 * | 4/2011 | Kalafut et al. | 600/431 |
| 2005/0113664 A1 * | 5/2005 | Stefani et al. | 600/407 |
| 2005/0249392 A1 * | 11/2005 | Allain et al. | 382/128 |

FOREIGN PATENT DOCUMENTS

| | | |
|---|---|---|
| JP | 2005261531 A | 9/2005 |
| JP | 2006198410 A | 8/2006 |
| WO | WO2006/058280 A2 * | 6/2006 |

OTHER PUBLICATIONS

Lynch et al. "Extraction of Epi-Cardium Contours from Unseen Images Using a Shape Database," IEEE NSS-MIC 2004 Medical Imaging Conference, Oct. 16-22, 2004, Rome, Italy.*
Dogan et al. "Right Ventricular Function in Patients with Acute Pulmonary Embolism: Analysis with Electrocardiography-synchronized Multi-Detector Row CT", Radiology, 242, 78-84, Jan. 2007.*
Unofficial translation of JPO Office Action for corresponding JP Application No. 2008-120053 dated Jan. 22, 2013.

* cited by examiner

*Primary Examiner* — Tse Chen
*Assistant Examiner* — Patricia Park
(74) *Attorney, Agent, or Firm* — Global Patent Operation

(57) ABSTRACT

A CT radiographic imaging process implements a processing operation on images in order to detect the use of a saline solution. When a saline solution is detected, it extracts a component or a portion of a component that does not appear to be contrasted in the initial images, for example, in the case of cardiac imaging, the right cavity of the heart. The imaging system comprises means for implementing this process.

7 Claims, 13 Drawing Sheets

CT TOMOGRAPHIC IMAGING PROCESS AND SYSTEM

BACKGROUND

1. General Technical Field of the Invention

This invention relates to CT tomographic imaging.

It is advantageously applied in cardiac imaging, but is not limited to this, and can also be applied in CT imaging of other organs.

2. Description of Prior Art

It is known that a conventional technique for acquiring images in CT tomography consists of injecting, in addition to the contrast product, a saline solution that is of higher density than the contrast product. If the acquisition is done on an organ—such as the heart, the saline solution pushes the contrast product into the cavities of the heart, and more specifically into the left cavity, thereby giving this cavity a greater contrast and a faster acquisition of images.

The images, which are thus clearer, have fewer artefacts, while the coronary artery is viewed with a very good contract.

However, this technique, which is now used by a large number of radiologists, has the major disadvantage of being incompatible with certain image processing operations conventionally performed following the acquisition (for example, and in a non-limiting manner for cardiac imaging: coronary analysis, functional analysis of the heart, detection of volumes, and so on).

Such processing operations indeed generally make it necessary to be capable of having a sufficient contrast. The segmentation of the heart requires, for example, a minimum contrast in each of the two cavities of the heart. However, the use of a saline solution tends to push all of the contrast product to the left cavity, and the right cavity is visible only with a much lower contrast. The resulting cardiac volume then does not contain the right cavities and coronary arteries.

FIG. 1 is a drawing of a cardiac image acquisition obtained with injection of a saline solution. This figure shows that the left cavity appears to be much more contrasted than the right cavity.

However, the current imaging system software is programmed today to systematically implement these post-processing operations, whether or not the practitioner needs to use saline solutions.

This results in a high error rate in the post-processing operations, which is unsatisfactory for practitioners.

SUMMARY OF THE INVENTION

An objective of the invention is therefore to overcome this disadvantage.

To this end, the invention proposes a CT radiographic imaging process, characterised in that a processing operation is implemented on the images in order to detect the use of a saline solution, and when a saline solution is detected, a processing operation is implemented in order to extract a component or a portion of a component that does not appear to be contrasted in the initial images.

In particular, in the case of a cardiac imaging process, the processing implemented extracts an image component corresponding to the right cavity of the heart.

To determine the use of a saline solution, it is possible to process the images so as to deduce the volume of the largest contrasted cardiac component of these images, as well as the bounding volume of this component and determine whether or not a saline solution has been used according to the ratio between these two volumes.

In addition, it is possible to determine the use of a saline solution as a function of the volume.

DESCRIPTION OF THE FIGURES

Other features and advantages of the invention will appear in the following description, which is illustrative and non-limiting, and which must be read in the light of the appended drawings, in which.

DETAILED DESCRIPTION

Review of CT Imaging Devices

Figure 1:
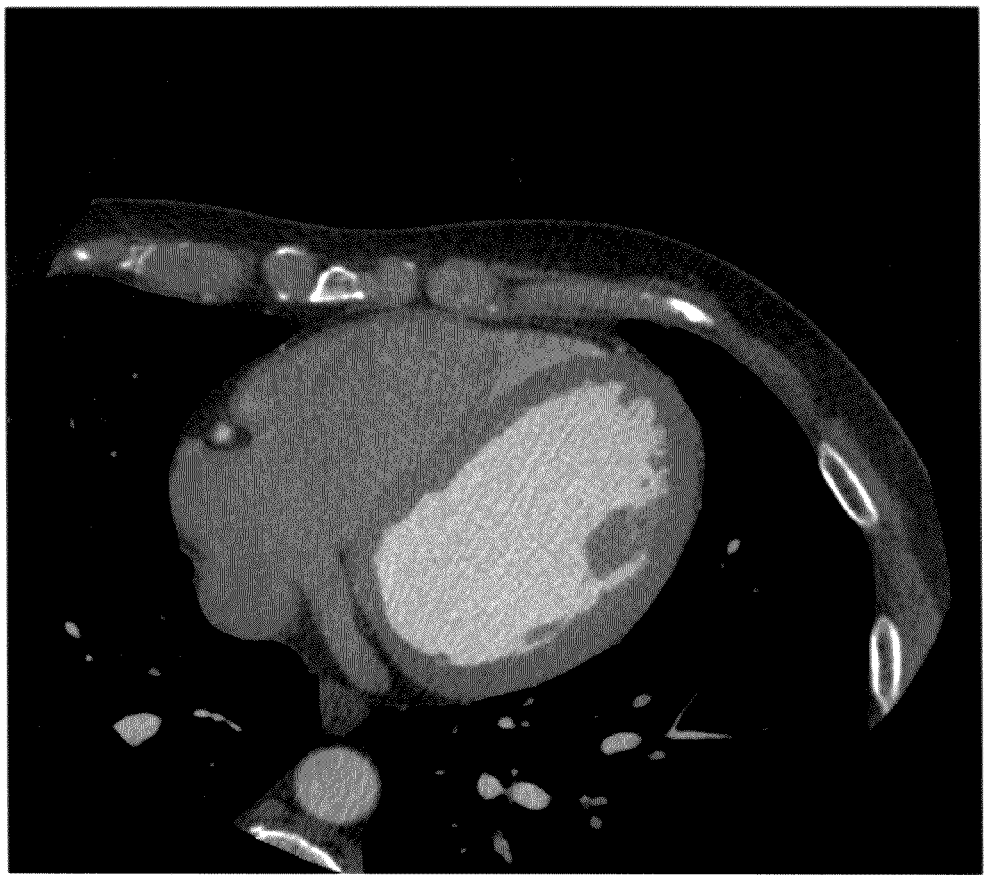
FIG. 1 (prior art), discussed above, shows an example of a 2D cross-section view obtained after injection of a saline solution.
Figure 2:
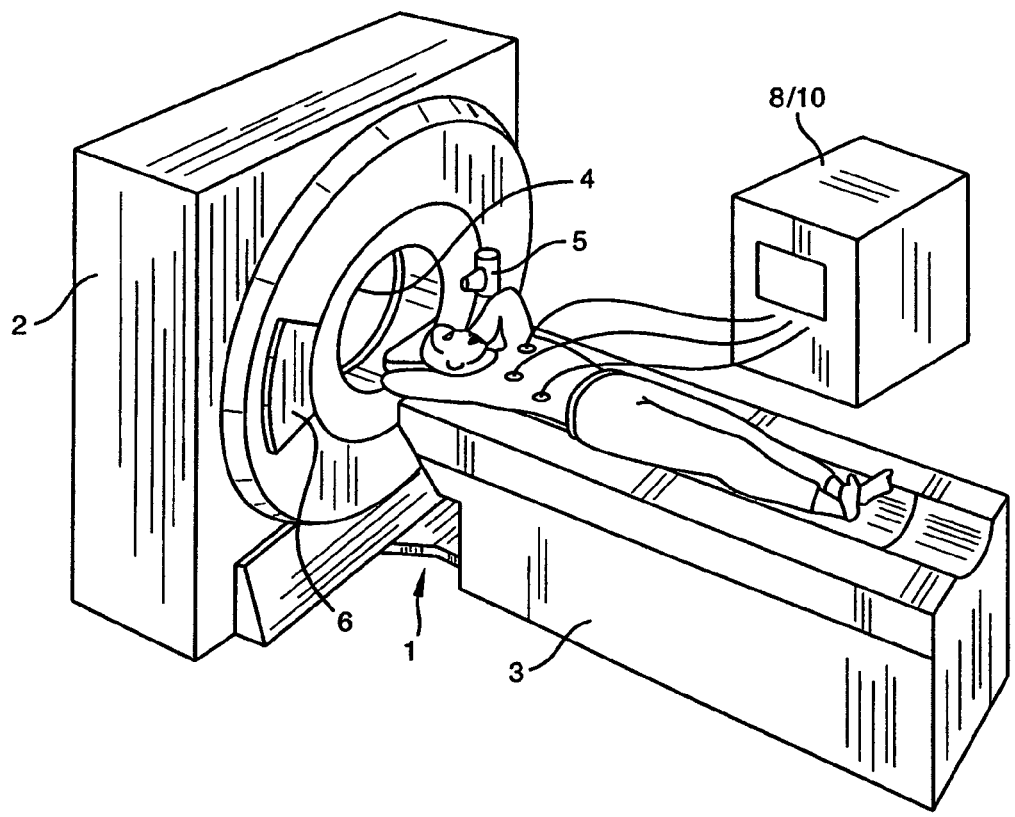
FIGS. 2 and 3 show a CT acquisition device.
Figure 3:
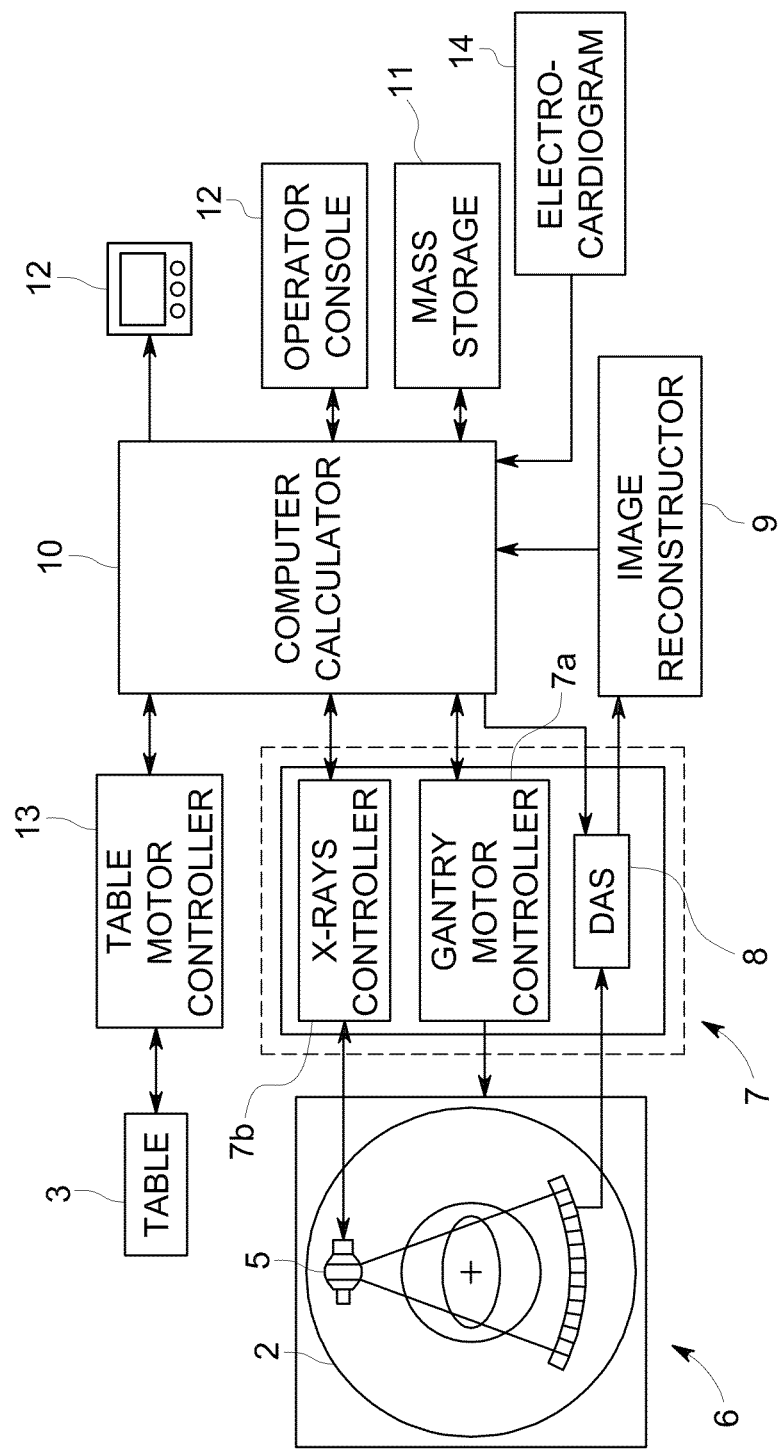

FIGS. 2 and 3 show an example of an imaging device 1.

Such a device conventionally comprises a frame 2 with a central opening 3 and a table 4 on which a patient can lie. The frame 2 includes a source 5 that transmits an X-ray beam toward the detection elements 6. When operating, the frame turns around its centre of rotation to enable a plurality of cross-sections to be obtained of the area of the patient to be examined.

Conventionally, such a device also comprises, as shown in FIG. 3, a control mechanism 7 that makes it possible to control the source 5 and the movement of the frame 2 (frame motor control 7a, X-ray control 7b). A data acquisition system 8 receives the analog signals at the output of the detection elements 6. This system 8 samples these signals and converts them into digital signals. An image reconstruction device 9 receives the data digitised by this system 8 and performs an image reconstruction processing operation on them. The images thus reconstructed are transmitted to a computer 10 that stores them in an associated storage unit 11 and implements a certain number of processing operations, including those described below. This computer 10 is also associated with interfaces 12 (console, keyboard, screen, etc.), which enable the practitioner to order and view the reconstructed and, as the case may be, reprocessed (3D images, 2D cross-sections) images. The computer 10 also communicates with a table motor control 13 that it controls, as well as with means 14 enabling the patient's electrocardiograms to be restored.

To implement the processing operations described below, the computer uses computer programs (software programs, packages, etc.), which store means for implementing the various steps of these processing operations. In general, these software programs and packages can be stored on any computer medium, and in particular in a non-limiting manner on disks, CD-ROMs, RAM memories, and so on.

General Algorithm Implemented by the Processing Means

We will consider a case in which a practitioner acquires cardiac images by means of such a CT imaging device.

To this end, the practitioner will inject contrast product into the person whose heart is being examined.

As the case may be, according to practice, a saline solution may also be injected into the patient, which will have the effect of pushing the contrast product.

Figure 4:
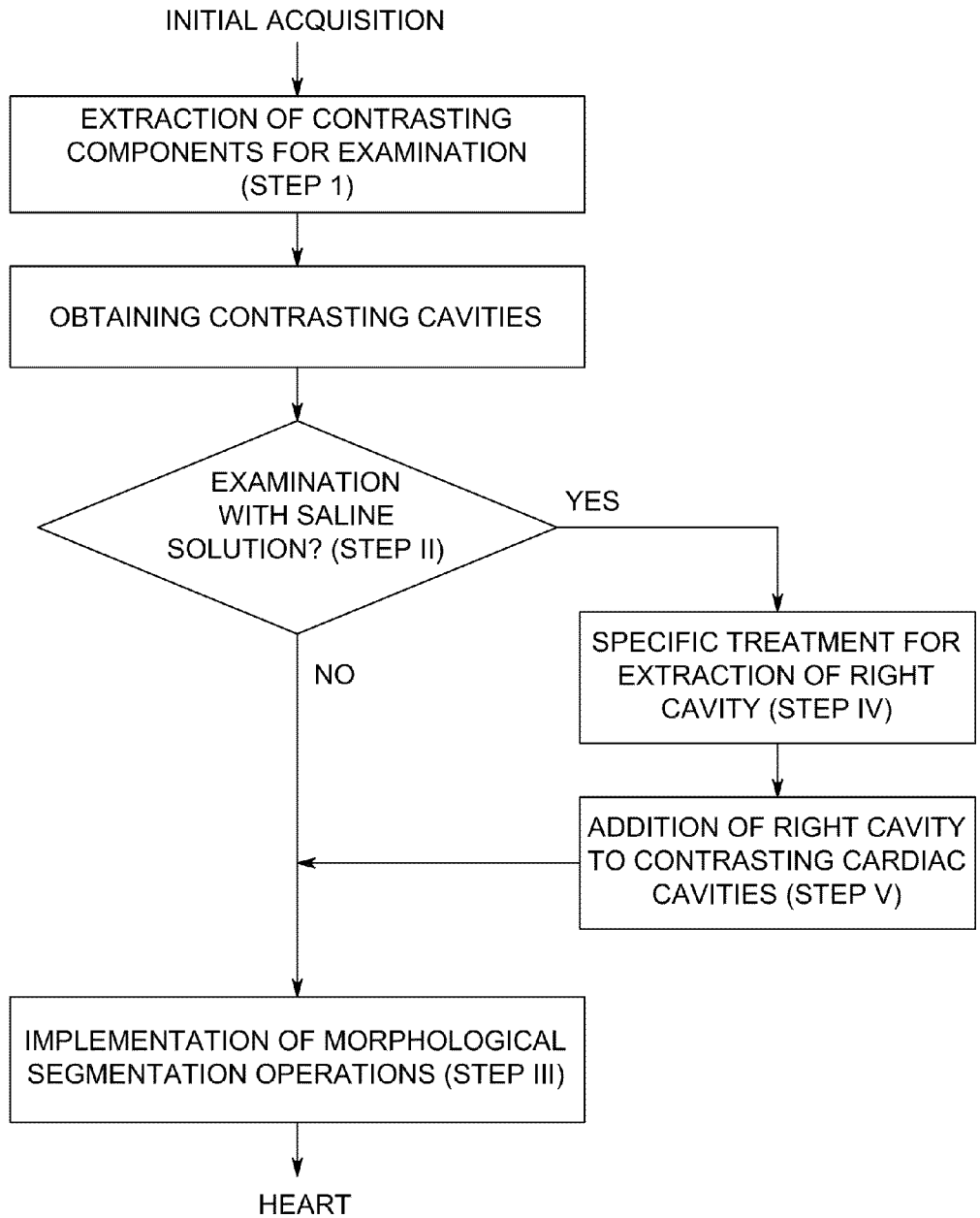
FIGS. 4 and 5 shows various steps of a processing process according to an embodiment of the invention.

The computer 10 of the imaging device manages the images thus acquired by implementing the various steps shown in FIG. 4.

In a first step (step I), once the practitioner has defined the cardiac volume on which he/she is to work, the processing means extract the contrasted components of the images corresponding to this volume. This extraction can be implemented, for example, by comparing the grey level of the images to a given threshold.

This first step makes it possible to isolate the contrasted cardiac cavities.

Figure 5:
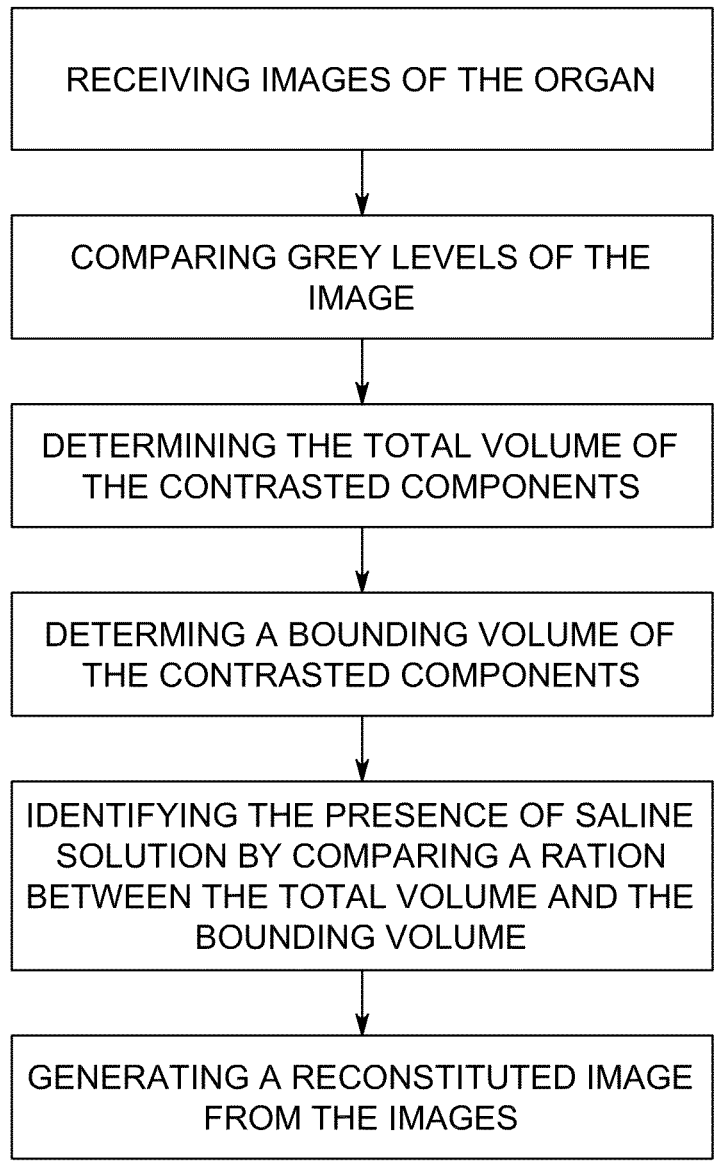

It can be understood, and as shown in FIGS. 5a and 5b, in the case of an examination with saline solution, the images comprise primarily a single contrasted component: that of the left cavities.

Determination of the Use of a Saline Solution by the Practitioner

Once the contrasted components have been isolated, tests are performed on them so as to enable the processing means to automatically determine whether or not the practitioner used a saline solution (step II).

To this end, the processing means determine the total volume of the contrasted components.

Figure 6A:
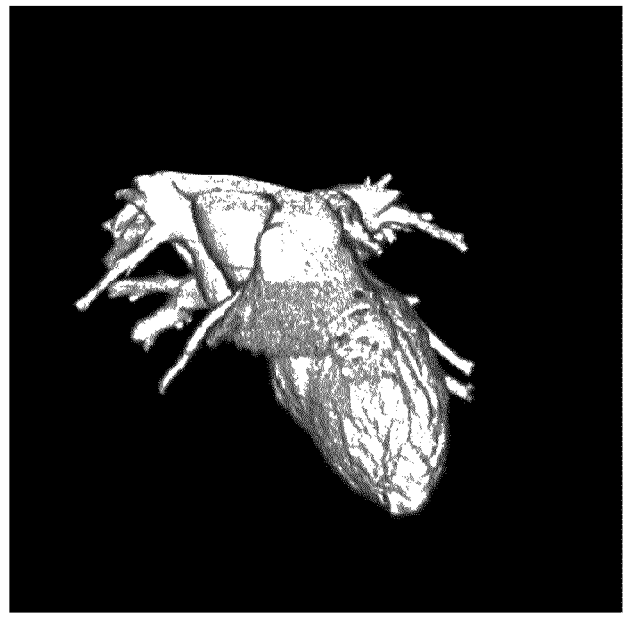
FIGS. 6a and 6b show a 3D view and a 2D cross-section of the largest contrasted cardiac component of a set of images obtained in the case of an examination with saline solution.
Figure 6B:
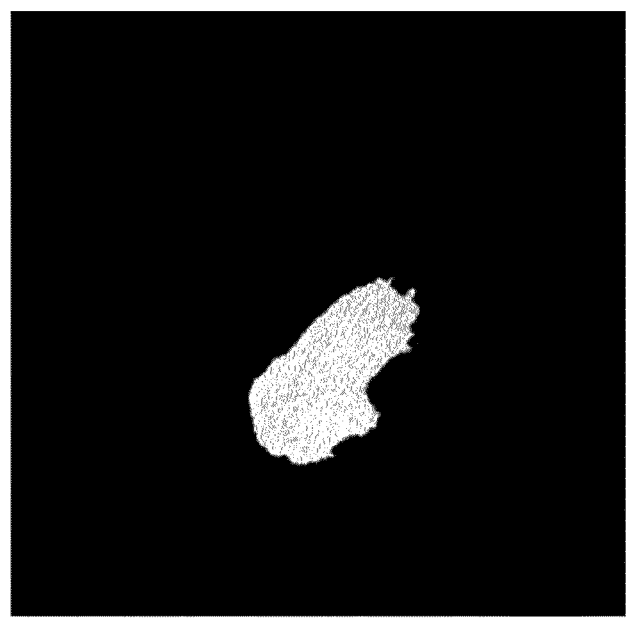

In addition, and as shown in FIG. 6, they determine the bounding volume of the contrasted cavities of the heart. To this end, these processing means identify the left cavities and identify the two end points A and B on said cavities.

Aside from the natural shape of a heart, the "bounding volume" can be similar to a cube, with the two end points A and B corresponding to the two ends of a diagonal of a median cross-section of said cube. The morphology of the heart indeed causes the bounding volume of the contrasted cardiac cavities to encompass not only the left cavities but also the uncontrasted right cavities, and some pulmonary veins. It is therefore possible to consider this "bounding volume" to be an approximation of the cardiac volume.

After identifying these two points A and B, the processing means reconstitute the bounding volume and determine its volume.

Figure 7:
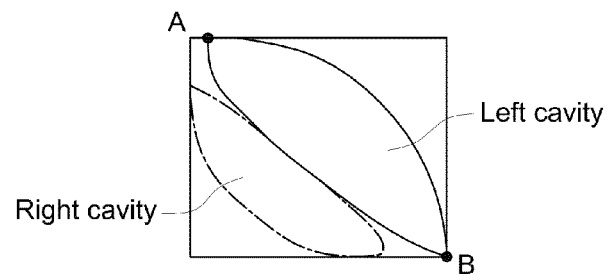
FIG. 7 (crown view) shows the determination of the bounding volume of the larges contrasted cavity.

The processing means (computer 10 and associated program(s)) implement a plurality of comparisons on the total volume of the contrasted components and on the bounding volume (FIG. 7).

In particular, they compare, to a threshold $S_{ratio}$, the ratio of the volume of the contrasted components over the volume of the bounding volume (comparison IIa).

They also compare, to a threshold $S_{ratio}$, the volume of the contrasted components (comparison IIb).

The processing means then determine that the examination is being performed with a saline solution when the ratio of the volumes and the volume of the contrasted components are both inferior to said two thresholds (result IIc). An examination with a saline solution is indeed characterised by a smaller contrasted cavity volume than for an examination without saline solution, and by a smaller "contrasted cavity volume" to "bounding volume" ratio.

It is noted that in the case of a small heart (cardiac examination of a child, for example), the volume of the contrasted cavities will be low in any case. The fact that a saline solution is not used will nevertheless be detected, since the "contrasted cavity volume" to "bounding volume" ratio will be greater than the threshold $S_{volume}$.

Of course, other selection criteria with these or with other parameters can be envisaged.

For example, the threshold $S_{ratio}$ can be on the order of 30% whereas the threshold $S_{volume}$ can be on the order of 600 cm$^3$.

At the end of these tests enabling the processing means to automatically determine whether or not the practitioner used a saline solution, the processing means implement conventional post-processing segmentation operations when no saline solution has been detected (step III in FIG. 2).

There are a wide variety of possible post-processing operations. They include, for example, the post-processing operations of coronary analysis, functional heart analysis, detection of volumes, and so on.

Such post-processing operations are conventionally known in themselves.

Extraction of the Right Cavity and Addition to the Left Cavity

When, on the other hand, a saline solution has been detected, the processing means implement a processing operation, described below, in order to extract the right cavity, which does not appear in the contrasted components of the images (step IV in FIG. 2).

To this end, the equipment implements a dilation processing operation on the recovered 3D images.

Figure 8:
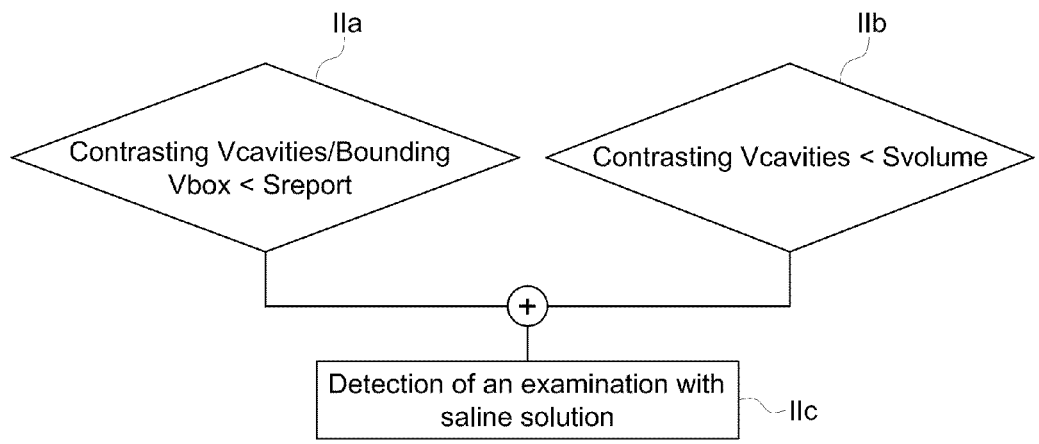
FIG. 8 shows the tests implemented so as to determine the use of a saline solution by the practitioner.

As shown in FIG. 8, this dilation processing consists of reconstituting the image shot-by-shot by completing, for each shot (in this case in FIG. 8, shot 1 to 2, where n is an integer), the contrasted components with the uncontrasted components, within the limits of a mask M enabling elements such as the lungs or bone elements to be removed.

A significant 2D dilation of the left cavities:
enables the right cavities to be extracted;
enables the right coronary arteries to be extracted;
prevents extracting too much of the liver located below the heart.

The mask is calculated automatically.

The use of the mask (initial volume without the lungs and pulmonary veins) makes it possible to avoid detecting the right or left pulmonary veins.

For examples of the principle of dilation calculation or mask calculation, reference can advantageously be made to the following general work:

SCHMITT M., MATTIOLI J. "Morphologie Mathématique", Masson, 1993.

Figure 9:
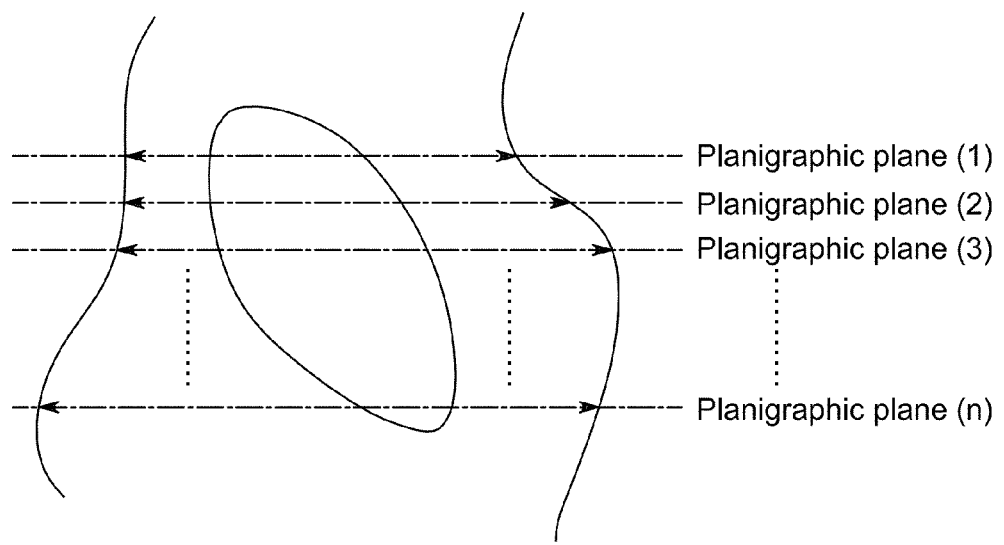
FIG. 9 shows the dilation processing in a mask implemented so as to enable an image of the right cavity to be recovered; (it seems unnecessary to redefine a dilation operation here)

This results in images of the type shown in FIGS. 9a and 9b.

Figure 10A:
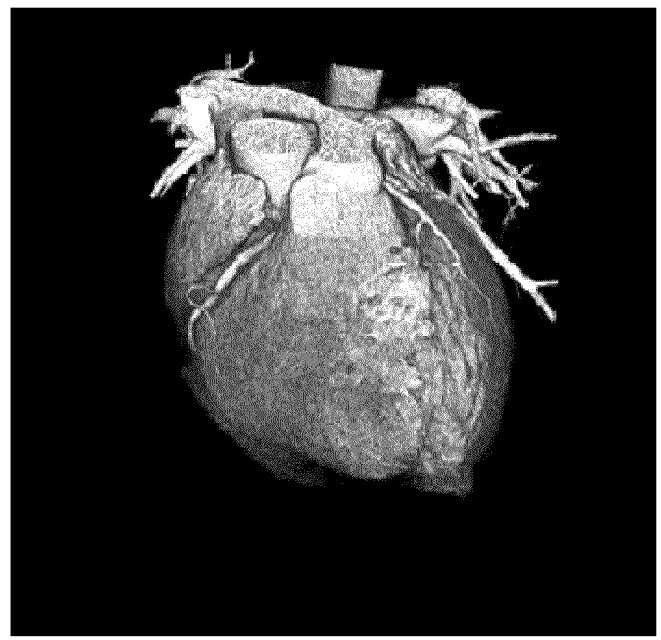
FIGS. 10a and 10b are a 3D view and a 2D cross-section obtained at the end of a dilation step.
Figure 10B:

After subtracting the image of the left cavity, images of the right cavity and possibly of other elements are obtained (FIG. 10a and 10b).

The reconstituted image thus obtained can be subjected to a thresholding or cleaning process. An additional step consists of deleting the unwanted detected elements: remaining pulmonary veins, descending aorta, vertebral column, and so on.

Figure 11A:
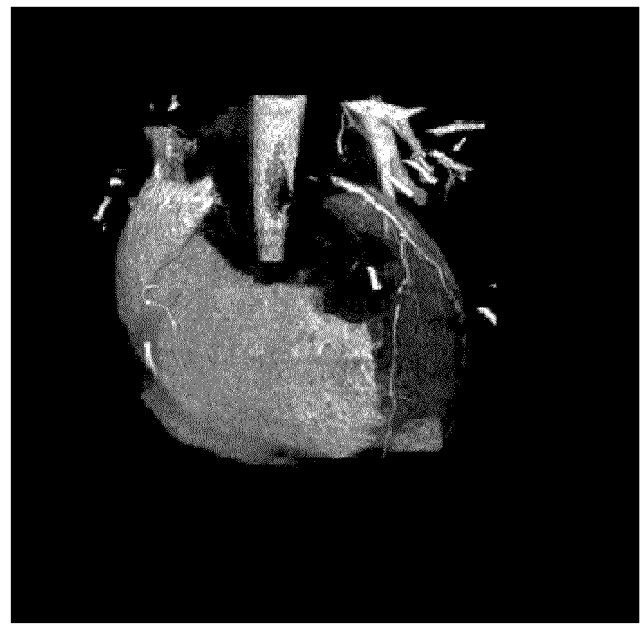
FIGS. 11a and 11b are a 3D view and a 2D cross-section obtained after subtracting the views of FIGS. 10a and 10b from the contrasted left cavity.
Figure 11B:
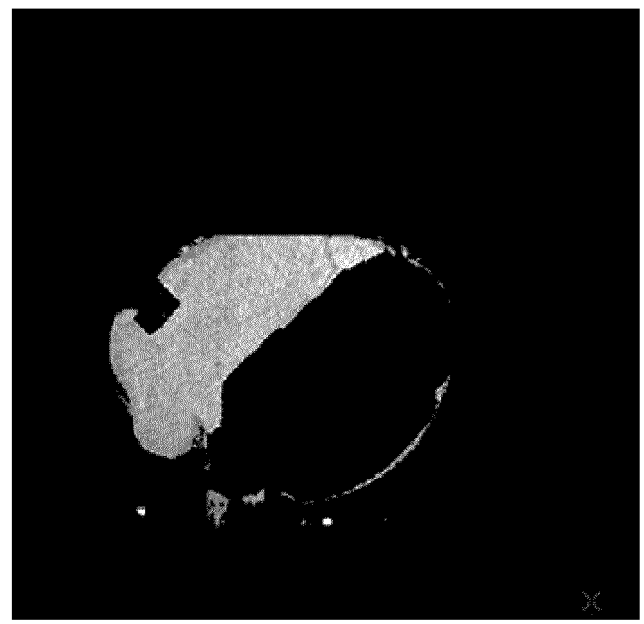
Figure 12:
FIGS. 12 and 13 are 2D cross-section views of the right cavity of FIG. 10b after a filtering processing and a morphology operation.
Figure 13:
Figure 14A:
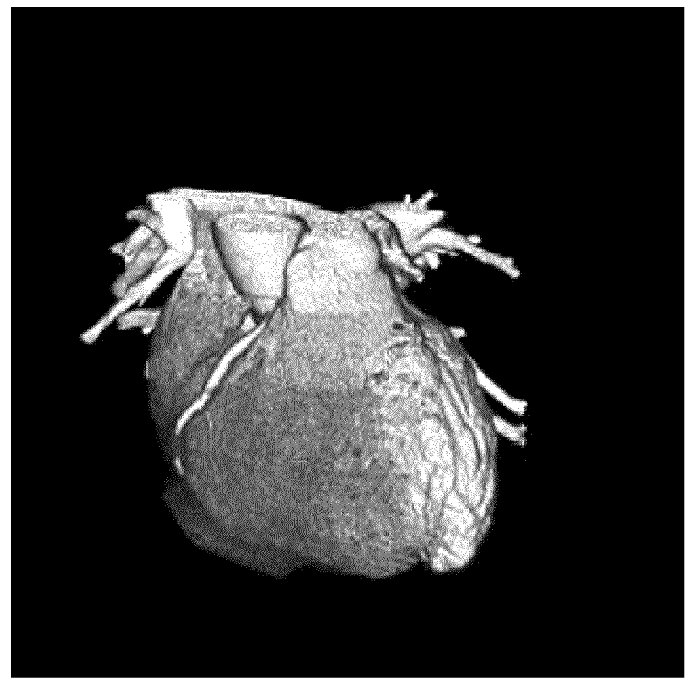
FIGS. 14a and 14b show a 3D view and a 2D cross-section as obtained after adding images of the right cavity and the left cavity.
Figure 14B:
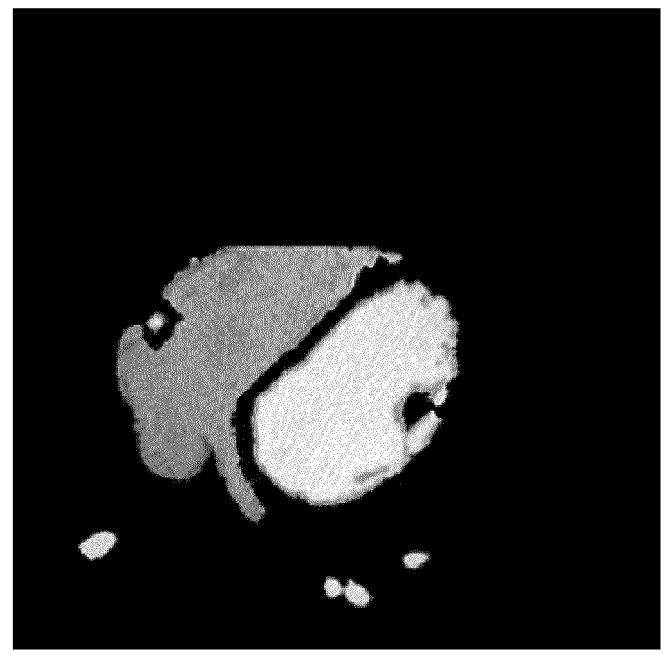

To do this, mathematical morphology operations (erosion, opening) are performed so as to keep only the largest related component, which corresponds to the right cavities (right ventricles and atrium) (FIGS. 11 and 12).

Such operations are also conventionally known in themselves.

It is possible in this regard also to refer advantageously to the general work mentioned above:

SCHMITT M., MATTIOLI J. "Morphologie Mathématique", Masson, 1993.

The component corresponding to the larges volume thus selected corresponds to the right cavity of the heart and is then added to the image of the left cavity (step V in FIG. 2).

This results in images of the two cavities of the heart, on which it is possible to implement the conventional segmenting operations.

The processing operation described above has been tested and enables detection in more than 85% of radiological examinations implemented with a saline solution.

Extraction of cardiac components has increased from 18% to 93%.

The success rates of angiographic views have increased from 12% to 82%.

The detection of coronary lines has increased from a success rate of 15% to a success rate of 70%.

The results for cases of processing operations without saline solution are remained unchanged.

A person skilled in the art can easily understand that the above description was provided in the context of a cardiac imaging application. However, the process and the system proposed can be similarly applied to the CT imaging of any other organ: liver, lungs and so on.

What is claimed is:

1. A method for processing images of an organ, said method comprising:
    at a computer comprising a computer program to implement image-processing operations:
    receiving an image of the organ;
    comparing grey levels of the image to a threshold value to identify a contrasted component of the organ, wherein the grey level of the contrasted component is greater than the threshold value;
    determining a total volume of the contrasted component;
    generating a bounding volume about the organ, wherein the bounding volume comprises a median cross-section of a cube having a diagonal with end points that correspond to a first point and a second point located on the periphery of the contrasted component;
    determining a total volume of the bounding volume:
    extracting a non-contrasted component from the image when a first ratio of the total volume of the contrasted component to the total volume of the bounding volume and the total volume of the contrasted component are less than, respectively, a first threshold value and a second threshold value;
    generating a reconstituted image comprising the contrasted component and the non-contrasted component.

2. The method for processing images of an organ of claim 1, wherein the organ is a heart and a component of the image includes a right cavity of the heart.

3. The method for processing images of an organ of claim 1, wherein the first threshold value is on the order of 30%.

4. The method for processing images of an organ of claim 1, wherein the second threshold value is on the order of 600 $cm^3$.

5. The method for processing images of an organ of claim 1, further comprising:
    calculating a mask; and
    performing a dilation processing operation in the mask to remove certain organs that are unnecessary to the image-processing operations.

6. The method for processing images of an organ of claim 5, further comprising configuring the mask to remove from the initial image pixels or voxels corresponding to a lung and a bone element of a vertebral column.

7. The method for processing images of an organ of claim 5, further comprising subtracting a volume of an initial contrasted component from the dilated images.

\* \* \* \* \*

UNITED STATES PATENT AND TRADEMARK OFFICE
CERTIFICATE OF CORRECTION

| | |
|---|---|
| PATENT NO. | : 8,489,173 B2 |
| APPLICATION NO. | : 12/151941 |
| DATED | : July 16, 2013 |
| INVENTOR(S) | : Pruvot et al. |

Page 1 of 1

It is certified that error appears in the above-identified patent and that said Letters Patent is hereby corrected as shown below:

In the Claims

In Column 6, Line 14, in Claim 1, delete "value;" and insert -- value; and --, therefor.

Signed and Sealed this
Fifteenth Day of October, 2013

Teresa Stanek Rea
*Deputy Director of the United States Patent and Trademark Office*